United States Patent [19]
Lin

[11] Patent Number: 5,575,791
[45] Date of Patent: *Nov. 19, 1996

[54] UNIVERSAL ECCENTRIC FIXATION MECHANISM FOR ORTHOPEDIC SURGERY

[76] Inventor: Chih-I Lin, 14292 Spring Vista La., Chino Hills, Calif. 91709

[*] Notice: The term of this patent shall not extend beyond the expiration date of Pat. No. 5,352,226.

[21] Appl. No.: 280,679

[22] Filed: Jul. 27, 1994

[51] Int. Cl.$^6$ .................................................. A61B 17/70
[52] U.S. Cl. ............................................................ 606/61
[58] Field of Search ............................... 606/61, 60, 73; 403/4

[56] References Cited

U.S. PATENT DOCUMENTS

| | | | |
|---|---|---|---|
| 4,420,272 | 12/1983 | Ingalls et al. | 403/4 |
| 5,176,680 | 1/1993 | Vignaud et al. | 606/61 |
| 5,306,275 | 4/1994 | Bryan | 606/61 |
| 5,352,226 | 10/1994 | Lin | 606/61 |

*Primary Examiner*—Gary Jackson
*Assistant Examiner*—Scott B. Markow
*Attorney, Agent, or Firm*—Bacon & Thomas

[57] ABSTRACT

A universal and eccentric fixation mechanism for an orthopedic surgery comprises a universal receiving seat, an eccentric collar, a rod body, and an urging and fixing element. The eccentric collar is received in a spherical hollow receiving seat of the universal receiving seat and provided with an urging slit. The eccentric collar has a hollow portion in which the rod body is held such that one end of the rod body is fastened with a bone fixing element. The slit of the eccentric collar can be urged to close by the urging and fixing element so that the rod body is held securely in the hollow portion of the eccentric collar. The hollow portion of the eccentric collar is cylindrical in shape and has an axis deviating from the spherical center of the eccentric collar of a spherical construction.

8 Claims, 3 Drawing Sheets

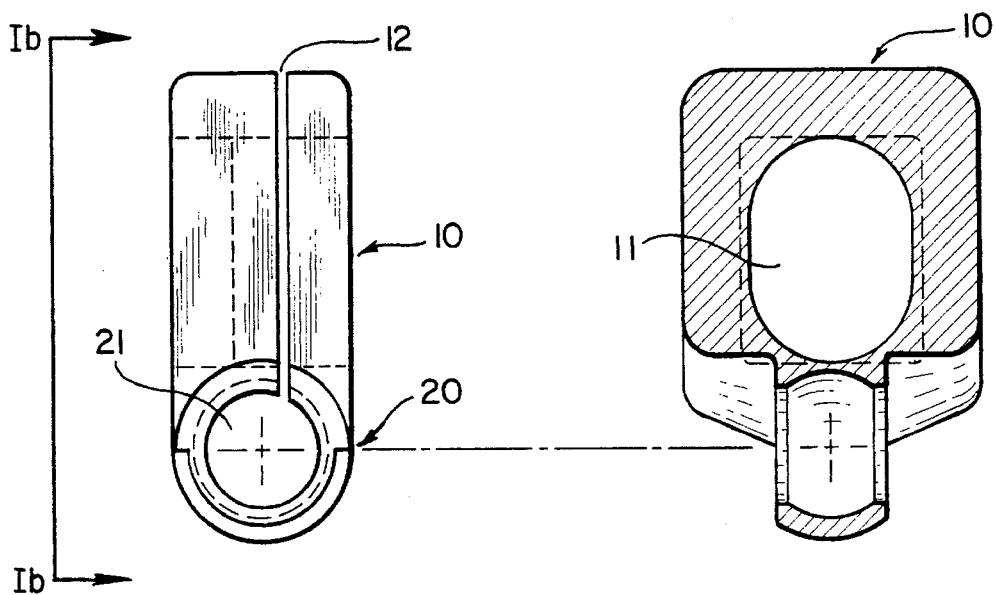
FIG. 1-a          FIG. 1-b
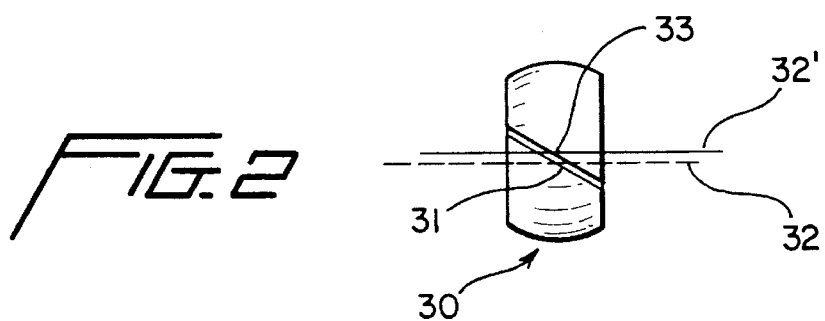
FIG. 2
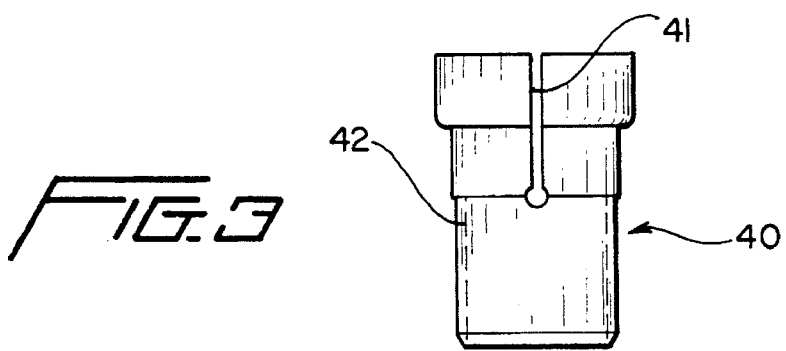
FIG. 3

UNIVERSAL ECCENTRIC FIXATION MECHANISM FOR ORTHOPEDIC SURGERY

FIELD OF THE INVENTION

The present invention relates generally to an orthopedic surgical device, and more particularly to a universal eccentric fixation mechanism for use in an orthopedic surgery for treating a deformed or injured vertebra.

BACKGROUND OF THE INVENTION

In view of the fact that a human spinal column is made up of a series of joined vertebrae, each of which has a specific curvature and a specific fixing direction, a surgical problem can often arise from the use of a vertebral fixation and retrieval system in fixing a vertebra under treatment. The Dimso Company, a French corporation, introduced the Diapason system which is disclosed in the U.S. Pat. No. 5,176,680 and is intended to provide a workable solution to the surgical problem arising from the use of the vertebral fixation and retrieval system. However, the Diapason system mentioned above is defective in design in that its fixation rod must be slightly curved in conformity with the curvature of a vertebra intended to be fixed. Such a surgical practice of curving the fixation rod of the Diapason system is in fact done in violation of the fixation principle of the spherical universal fixation device, thereby resulting in a poor fixation effect. In addition, the Dispason system is practically useless unless the bone screw and the fixation rod are so located that they are not far apart from each other.

The shortcomings of the Diapason system can be overcome by a universal fixation mechanism introduced by this inventor of the present application and disclosed in U.S. Pat. No. 5,352,226. However, the afore-mentioned universal fixation mechanism is limited in design in that it does not provide a workable solution to a minor surgical correction that must be done at such time when the fastening position of the bone screw is caused to deviate slightly.

SUMMARY OF THE INVENTION

It is therefore the primary objective of the present invention to provide a universal eccentric fixation mechanism, which is capable of carrying out a fixation effect in all directions and which permits an operating surgeon to do a minor correction or remedy at such time when the fastening position of a bone screw is caused to deviate.

It is another objective of the present invention to provide a universal eccentric fixation mechanism, which can be used in place of the vertebral fixation and retrieval system as well as other bone fixing systems.

It is still another objective of the present invention to provide a universal eccentric fixation mechanism, which has a universal adjustment effect.

It is still another objective of the present invention to provide an orthopedic universal fixation mechanism, which is eccentric.

It is still another objective of the present invention to provide a universal eccentric fixation mechanism, which is composed of a universal receiving seat, an eccentric collar, an urging and fixing element, and a rod body.

The universal receiving seat is of a hollow construction and has an interior which is slightly spherical in shape.

The eccentric collar is so spherical in shape as to fit into the spherical hollow seat of the universal receiving seat. The eccentric collar has an urging slit.

The rod body is located in the hollow portion of the eccentric collar such that one end of the rod body is coupled with other bone fixing element.

The urging and fixing element urges directly the eccentric collar from the outside of the universal receiving seat so as to seal off the urging slit of the eccentric collar, thereby causing the eccentric collar to hold securely the rod body which is located in the hollow portion of the eccentric collar.

The universal eccentric fixation mechanism of the present invention is characterized in that the hollow portion of the eccentric collar is slightly cylindrical in shape and has an axis deviating from the center of the eccentric collar of the spherical construction.

The component parts of the universal eccentric fixation mechanism of the present invention may be made of biocompatible and implantable materials, such as the iron-based stainless steel 316 LVM, the titanium-based Ti-6-4, the cobalt-molybdenum-chromium alloy, etc., which are all suitable for use in the orthopedic treatment of a deformed or injured bone.

The universal receiving seat of the universal eccentric fixation mechanism of the present invention is employed in such a manner that it is fastened with other bone fixing element, such as a bone screw, a lateral fixation block, or other element similar to the bone fixing element. If the universal receiving seat is fastened with the bone screw, the system so formed is similar to the Diapason system disclosed in the U.S. Pat. No. 5,176,680. However, according to the system of the present invention, the fastening position of the vertebral fixation rod and the eccentric collar can be so adjusted that a nonaligned bone screw can be also fastened with the vertebral fixation rod without causing the vertebral fixation rod to curve appropriately. In other words, according the system of the present invention, the distance that the vertebral fixation rod deviates from the axis of the hollow portion of the eccentric collar can be so adjusted as to permit a nonaligned bone screw to be fastened to the vertebral fixation rod. If the universal receiving seat is fastened with the lateral fixation block, the system so formed is similar to the lateral universal fixation system disclosed in the U.S. Pat. No. 5,352,226, which was filed by this inventor of the present application. However, according to the present invention, the position and the angle of the rod body (including the bone fixing element fastened thereto) can be adjusted or corrected by adjusting the position of the rod body held in the hollow portion of the eccentric collar.

With the exception of the two open ends of the hollow receiving seat of the universal receiving seat of the present invention, the hollow receiving seat is of a spherical construction. Such a hollow spherical construction can be formed by the universal receiving seat and the urging and fixing element. For example, the Diapason system is a case in point. The hollow spherical construction can be also formed by the universal receiving seat and other bone fixing element fastened to the universal receiving seat. For instance, the afore-mentioned lateral universal fixation system is a case in point.

The rod body of the present invention may be the rod-shaped portion of a bone fixing element, such as the main portion of a vertebral fixation rod, the handle portion of a bone screw or hook, the main body of a vertebral auxiliary fixation rod, etc.

With the exception of the both open ends, the eccentric collar of the present invention has a spherical profile and an outer diameter which is substantially equal to the inner diameter of the hollow spherical portion of the universal receiving seat. The hollow portion of the eccentric collar may be of any shape as long as the hollow portion is so dimensioned as to receive therein appropriately the top portion of a bone screw or a device similar to the bone screw. Generally speaking, the hollow portion of the eccentric collar is preferably and slightly cylindrical in shape. The eccentric collar is provided with an urging slit, which is preferably disposed such that the slit penetrates from the outer portion of the collar toward the inner portion of the collar. The slit is preferably oblique in direction.

The fixation mechanism of the present invention is eccentric and universal in view of the fact that the axis of the cylindrical hollow portion of the eccentric collar deviates from the spherical center of the eccentric collar. In other words, the axis of the cylindrical hollow portion of the eccentric collar deviates from the spherical center of the spherical universal receiving seat of the universal fixation block.

The urging and fixing element of the present invention may be any conventional urging and fixing element, such as a nut urging and fixing element, for urging the urging slit of the lateral fixation block so as to cause the lateral fixation block to clamp securely the vertebral fixation rod and to compress the universal receiving seat of the universal fixation block. As a result, the eccentric collar is so urged that a bone screw received therein is fixed securely.

For example, the universal eccentric fixation mechanism of the present invention is composed of a lateral fixation block and a universal receiving seat, which form together a hollow spherical receiving seat. In addition, the eccentric collar serves as a universal joint, thereby permitting a bone screw, which is received in the eccentric collar, to be adjusted freely in any desired direction. Furthermore, the fastening position of the bone screw can be slightly corrected by adjusting the position of the bone screw handle in the hollow portion of the eccentric collar. Such a surgical maneuver as described above can be attained in view of he fact that the axis of the hollow portion of the eccentric collar deviates from the spherical center of the hollow spherical receiving seat of the universal receiving seat. As soon as the bone screw is fastened correctly onto a vertebra intended to be fixed, the urging and fixing element is tightened so as to locate the bone screw in the vertebra.

The foregoing objectives, features, functions, and advantages of the present invention will be more readily understood upon a thoughtful deliberation of the following detailed description of the embodiments of the present invention in conjunction with the accompanying drawings.

BRIEF DESCRIPTION OF THE DRAWINGS

FIGS. 1A and 1B comprise FIG. 1-a is a top plan view of that the universal receiving seat of the present invention coupled in with the lateral fixation block to form the lateral universal fixation member.

FIG. 1-b is a side view generally taken in the direction of line Ib—Ib of FIG. 1 with a portion of the universal fixation member being broken away for illustrative purposes.

FIG. 2 shows a schematic view of the eccentric collar of the present invention.

FIG. 3 shows a schematic view of the urging and fixing element (not including the urging nut) of the present invention.

DETAILED DESCRIPTION OF THE EMBODIMENTS

Figure 4:
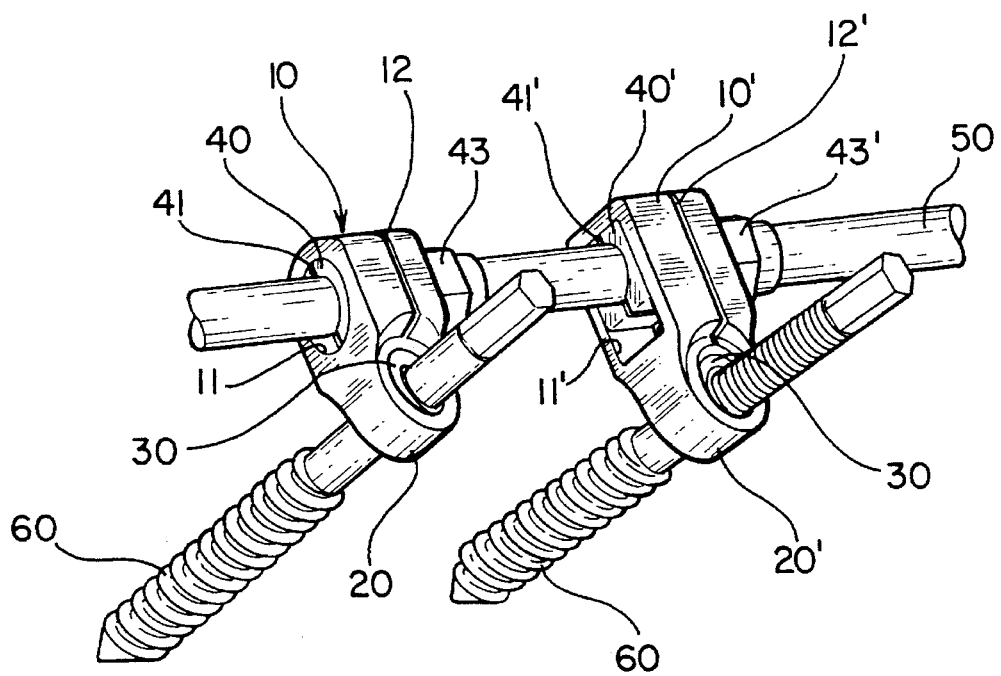
FIG. 4 shows a perspective view of the present invention in combination.

As shown in FIG. 1, the present invention is made up of a lateral fixation block 10 and a universal receiving seat 20. The lateral fixation block 10 is provided with a through hole 11 and an urging slit 12. The universal receiving seat 20 is provided with a hollow spherical receiving seat 21. FIG. 1-a is a top plan view of the present invention while FIG. 1-b is a side view taken along the direction indicated by a line Ib—Ib in FIG. 1-a with a portion of the universal fixation member broken away for illustrative purposes.

As shown in FIG. 2, the present invention comprises an eccentric collar 30 provided with an urging slit 31, and with a cylindrical hollow portion having a central axis represented by dotted line 32 which is offset from a longitudinal centerline 32', and the spherical center 33 of eccentric collar 30.

Another aspect of the present invention is illustrated in FIG. 3, in which the present invention is shown to comprise an urging and fixing element 40 provided with a slit 41 and a threaded portion 42.

The present invention in combination is illustrated in FIG. 4, in which the reference numerals of 10, 11, 20, 30, 40 and 41 are similar in definition to the like reference numerals of FIGS. 1, 2 and 3, and in which the present invention is shown to combine with an urging nut 43, a vertebral fixation rod 50, and a bone fixing element in the form of a bone screw 60 in the left side portion of this figure. The embodiment illustrated on the right side portion of this figure is substantially identical with like reference numerals referring to corresponding parts except that urging and fixing element 40' constitutes a cubic hollow block received in a correspondingly shaped hole 11'.

Figure 5:
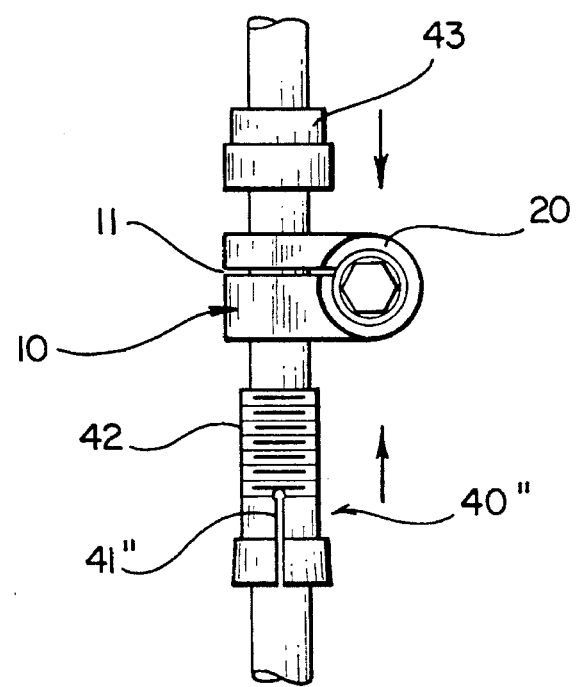
FIG. 5 is a schematic view showing the way by which the lateral universal fixation system as shown in FIG. 4 is caused to urge.

The reference numerals of 10, 11, 20, 41 and 43 of FIG. 5 are similar in definition to the like numerals of FIG. 4. The urging and fixing element 40" is provided with threads 42. As the urging and fixing element 40" is caused to advance in the direction indicated by an arrow, the threads 42 and the nut 43 are caused to engage each other so as to urge the slit 41" of the urging and fixing element 40". As the slit 41 is forced to close, the urging and fixing element 40" and the vertebral fixation rod 50 are fastened together securely.

Figure 6:
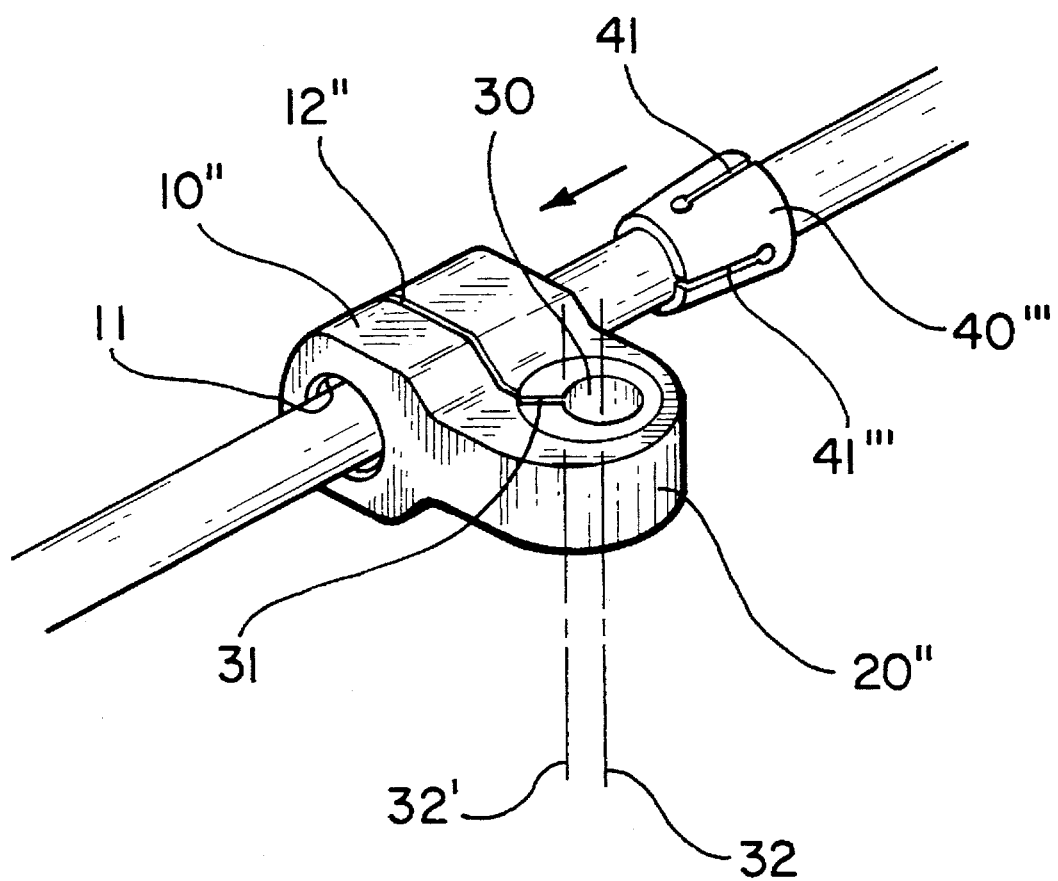
FIG. 6 is a partial perspective view showing that the present invention may comprise an urging and fastening element provided with a plurality of slits.

The numerals of 10", 12", 20", 30 and 31 of FIG. 6 are similar in definition to the like numerals of FIGS. 1–4. The urging and fixing element is replaced by a collar 40" having slits 41 and 42. The collar 40" has a bevel of an inclination of about 3°. As a result, the collar 40" can not be forced out at the time when the collar 40" is inserted into a through hole 11" of the lateral fixation block 10" so as to urge the universal eccentric fixation mechanism of the present invention.

On the basis of the embodiments described above, it is readily apparent that the angle at which the bone screw 60 is fastened onto a vertebra can be adjusted freely as desired in view of the universal receiving seat 30 and the eccentric collar which are united in a manner similar to a universal joint before the lateral fixation block is urged by the urging and fixing element. However, after the lateral fixation block is urged by the urging and fixing element, the slit of the lateral fixation block is forced to close so as to cause the universal receiving seat to clamp securely the eccentric collar of the spherical construction. As a result, the slit of the eccentric collar is also forced to close so as to clamp securely the bone screw. The lateral universal fixation system in its entirety, the bone screw, and the vertebral fixation rod are therefore fastened together securely.

The embodiments of the present invention described above are to be regarded in all respects as merely illustrative and not restrictive. Accordingly, the present invention may be embodied in other specific forms without deviating from the spirit thereof. The present invention is therefore to be limited only by the scope of the following appended claims.

What is claimed is:

1. A universal eccentric fixation mechanism for orthopedic surgery comprising:

a lateral fixation block including a first portion provided with a through hole adapted to receive a vertebral fixation rod and a second portion defining a universal receiving seat provided therein with a hollow receiving seat of a spherical construction, the first portion of said lateral fixation block including a slit that leads to said universal receiving seat such that said lateral fixation block has first and second sections split by said slit and interconnected by said universal receiving seat;

an eccentric collar of a spherical construction and dimensioned to fit into said hollow receiving seat of said universal receiving seat, said eccentric collar having a hollow portion and an urging slit extending through said eccentric collar to said hollow portion, said eccentric collar having a central longitudinal axis that passes through a spherical center thereof;

a bone fixing element having a first portion held in the hollow portion of said eccentric collar and a second portion adapted to be secured to a bone; and an urging and fixing means for urging the first and second sections of said lateral fixation block together and indirectly forcing said eccentric collar towards a substantially closed position so that said bone fixing element is held securely and intimately in said hollow portion of said eccentric collar;

wherein said hollow portion of said eccentric collar is cylindrical in shape and has an associated longitudinal axis that is offset from said central longitudinal axis of said eccentric collar.

2. The universal eccentric fixation mechanism according to claim 1 wherein said urging slit is arranged at an angle to said central longitudinal axis of said eccentric collar.

3. The universal eccentric fixation mechanism according to claim 1 wherein said bone fixing element comprises a bone screw.

4. The universal eccentric fixation mechanism according to claim 1 wherein said urging and fixing means includes an urging and fixing element that is received within the through hole provided in the first portion of said lateral fixation block.

5. The universal eccentric fixation mechanism according to claim 4 wherein said urging and fixing element is provided with threads and said urging and fixing means further comprises a threaded nut adapted to be threadably engaged with the threads of said urging and fixing element.

6. The universal eccentric fixation mechanism according to claim 4 wherein said urging and fixing element comprises a slitted collar.

7. The universal eccentric fixation mechanism according to claim 6 wherein said collar is provided with at least two circumferentially spaced slits.

8. The universal eccentric fixation mechanism according to claim 7 wherein said at least two circumferentially spaced slits extend into said collar from different longitudinal ends of said collar.

* * * * *